US00PP08818P

United States Patent [19]

Schumann

[11] Patent Number: Plant 8,818

[45] Date of Patent: Jul. 5, 1994

[54] GERANIUM PLANT NAMED FISCASA

[75] Inventor: Ingeborg Schumann, Albstadt, Fed. Rep. of Germany

[73] Assignee: Florfis AG, Binningen, Switzerland

[21] Appl. No.: 94,324

[22] Filed: Jul. 21, 1993

[51] Int. Cl.[5] ..... A01H 5/00

[52] U.S. Cl. ..... Plt./87.12

[58] Field of Search ..... Plt. 87.12

*Primary Examiner*—James R. Feyrer

*Attorney, Agent, or Firm*—Foley & Lardner

[57] ABSTRACT

A new and distinct cultivar of geranium named Fiscasa, particularly characterized by the combined features of light pink flower color, semi-double flower type, large umbels with long peduncles, medium green foliage with weak zonation, vigorous growth, early spring flower response, and rich flowering throughout the year.

1 Drawing Sheet

1

The present invention comprises a new and distinct cultivar of geranium, botanically known as *Pelargonium zonale l'hert,* and hereinafter referred to by the cultivar name Fiscasa.

Fiscasa is a product of planned breeding program which had the objective of creating new geranium cultivars with light salmon pink flower color, medium green foliage, vigorous growth, and good branching ability.

Fiscasa was originated from a hybridization made by inventor Ingeborg Schumann in a controlled breeding program in Galdar, Gran Canaria, Spain in 1987. The female parent was a result of a selfing of a hybrid produced from crosses between the cultivars Purlapen Dresden Doll White and Summercloud. Purlapen, disclosed in U.S. plant Pat. No. 5054 under the varietal name Veronika, has red purple flowers, medium growth, leaves with weak zonation, and early spring flower response. Dresden Doll White has single white flowers, medium green foliage without zonation, and medium plant habit. Summercloud is characterized by white semi-double flowers, tall plant habit and leaves without zonation. The male parent of Fiscasa was the patented variety Blues, disclosed in U.S. plant pat. No. 5373, and having pink semi-double flowers with red eyes on petals, short plant habit and early spring flower response.

Fiscasa was discovered and selected as one flowering plant within the progeny of the stated cross by Ingeborg Schumann in 1988 in a controlled environment in Galdar, Gran Canaria, Spain.

The first act of asexual reproduction of Fiscasa was accomplished when vegetative cuttings were taken from the initial selection in February 1989 in a controlled environment in Galdar, Gran Canaria, Spain, by, or under the supervision of, Ingeborg Schumann.

Horticultural examination of plants grown from these cuttings initiated in May 1989, and continuing thereafter, has demonstrated that the combination of characteristics as herein disclosed for Fiscasa are firmly fixed and are retained through successive generations of asexual reproduction.

Fiscasa has not been observed under all possible environmental conditions. The phenotype may vary significantly with variations in environment such as temperature, light intensity and day length without, however, any variation in genotype. The following observations, measurements, and comparisons describe plants grown in Hillscheid, Federal Republic of Germany under

2 greenhouse conditions which approximate those generally used in commercial practice.

The following traits have been repeatedly observed and are determined to be basic characteristic of Fiscasa, which in combination distinguish this geranium as a new and distinct cultivar:

1. Light pink semi-double flowers
2. Petals have a white eye at the base
3. Large umbels with long peduncles
4. Medium green foliage with very weak zonation
5. Vigorous growth
6. Early spring flower response
7. Abundant flowering throughout the year Of the many commercial cultivars known to the present inventor, the most similar in comparison to Fiscasa is Fispia. Reference is made to attached Chart A which compares certain characteristics of Fiscasa to those same characteristics of Fispia. In general comparison to Fispia, Fiscasa has a pink flower color with less bluish tint, more vigorous growth, larger umbels and longer peduncles.

The accompanying color photographic drawing shows typical flower and foliage characteristics of Fiscasa, with colors being as true as possible with illustrations of this type.

In the following description color references are made to The Royal Horticultural Society Colour Chart. The color values were determined indoors in May from plants grown indoors in Hillscheid, Federal Republic of Germany.

Classification:

*Botanical.*—A Hybrid of the species *Pelargonium zonale l'Hert.*

*Commercial.*—Zonal geranium, cv., Fiscasa.

INFLORESCENCE

A. Umbel:

*Shape.*—Semi-spherical.

*Average diameter.*—120 mm.

*Average depth.*—60 mm.

*Peduncle length.*—240 mm.

*Peduncle color.*—Light green.

*Pedicel length.*—22 mm.

*Pedicel color.*—Green infused with light red.

*Number of flowers per umbel*—40–50.

B. Corolla:

*Average diameter.*—48 mm.

*Form*—Semi-double.
*Number of petals.*—6–9.
*Number of petaloids.*—1–2.
*Color (general tonality from a distance of three meters).*—Light pink.
*Color of upper petals.*—65 A/B.
*Color of lower petals.*—65 A/B.
*Markings, mainly on upper petals.*—White zone at the base.
*Color of lower surface of petals.*—65 C/D.
*Color of sepals.*—Light Green.
*Number of sepals.*—5.

C. Bud:
*Shape.*—Elliptic.
*Color (adaxial).*—Light green.
*Color (abaxial).*—Light pink.

D. Reproductive organs:
*Androecium.*—7–10 fertile anthers; white filaments and orange pollen.
*Gynoecium.*—5–6 lobed stigma, white style and pink stigma.

E. Spring flowering response period: In Hillscheid, Federal Republic of Germany, in 1993 plants had on average 1.7 flowers opened 10 weeks after planting of unrooted cuttings.

F. Outdoor flower production: The flower count in 1992 in Hillscheid, Federal Republic of Germany was between 40 and 45 flowers per plant for May through August observation period.

G. Durability: Shatter resistance good.

PLANT

A Foliage:
*Form.*—Kidney-shaped.
*Margin.*—Bicrenated.
*Size of leaf.*—10–12 cm.
*Color of upper surface.*—Medium green, approximately 137 D.
*Color of zonation.*—Deeper green, approximately 137A/B.
*Tolerance of botrytis*—Average.

B. General appearance and form:
*Internode length.*—30–45 mm.
*Branching pattern.*—3.4 branches per week.
*Height (12 week old plants).*—19 cm.

CHART A

| CHARACTERISTIC | FISCASA | FISPIA |
|---|---|---|
| Flower color | 65 A/B | Between 73C and 75C |
| Number of petals | 7–10 | 6–8 |
| Plant height | 19 cm | 14 cm |
| Internodes | 30–45 mm | 15–35 mm |

I claim:

1. A new and distinct cultivar of geranium plant named Fiscasa, as illustrated and described.

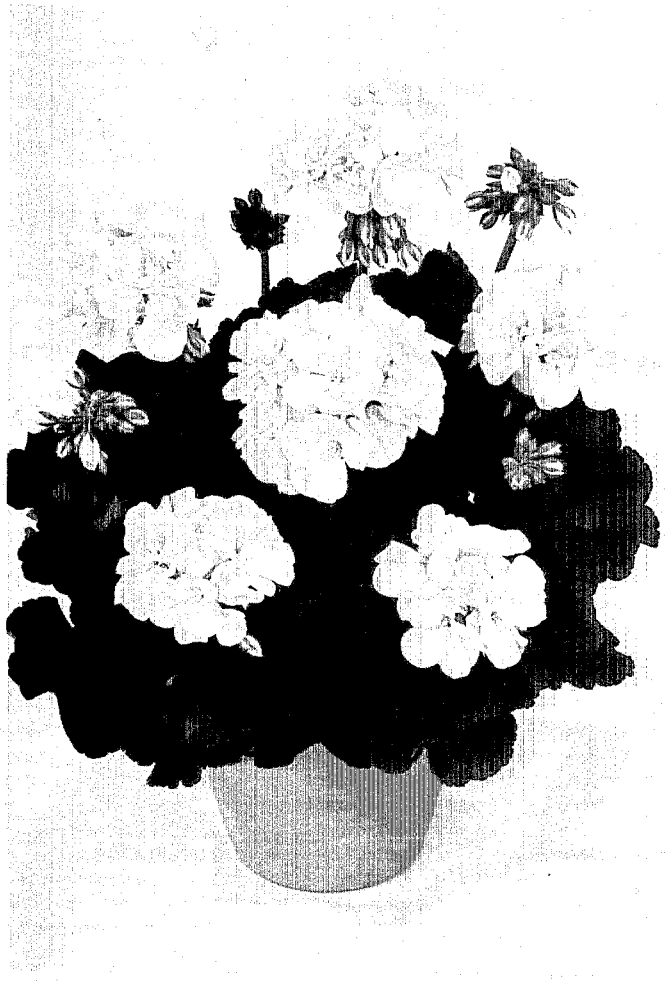

* * * * *